US008961563B2

(12) United States Patent
Vannemreddy

(10) Patent No.: US 8,961,563 B2
(45) Date of Patent: Feb. 24, 2015

(54) ANTERIOR ATLANTOAXIAL STABILIZATION BY LATERAL MASS SCREW FIXATION

(76) Inventor: Prasad Vannemreddy, Chicago, IL (US)

(*) Notice: Subject to any disclaimer, the term of this patent is extended or adjusted under 35 U.S.C. 154(b) by 0 days.

(21) Appl. No.: 13/466,862

(22) Filed: May 8, 2012

(65) Prior Publication Data

US 2013/0110167 A1    May 2, 2013

Related U.S. Application Data

(60) Provisional application No. 61/628,173, filed on Oct. 26, 2011.

(51) Int. Cl.
*A61B 17/70* (2006.01)

(52) U.S. Cl.
USPC .......................................................... 606/246

(58) Field of Classification Search
USPC .............. 606/280, 70, 71, 281–286, 299, 301
See application file for complete search history.

(56) References Cited

U.S. PATENT DOCUMENTS

| | | | |
|---|---|---|---|
| 4,572,039 A | 2/1986 | Desjardins | |
| 5,085,660 A | 2/1992 | Lin | |
| 5,352,229 A | 10/1994 | Goble et al. | |
| 5,364,399 A | 11/1994 | Lowery et al. | |
| 5,423,826 A | 6/1995 | Coates et al. | |
| 5,603,713 A | 2/1997 | Aust et al. | |
| 5,718,705 A | 2/1998 | Sammarco | |
| 6,916,320 B2 | 7/2005 | Michelson | |
| 7,074,221 B2 | 7/2006 | Michelson | |
| 2002/0143328 A1 | 10/2002 | Shluzas et al. | |
| 2005/0216010 A1 | 9/2005 | Michelson | |
| 2006/0189990 A1 | 8/2006 | Farris et al. | |
| 2006/0241614 A1 | 10/2006 | Bruneau et al. | |
| 2006/0241616 A1 | 10/2006 | Konieczynski et al. | |

FOREIGN PATENT DOCUMENTS

DE    19834326 A1 *    2/2000

OTHER PUBLICATIONS

C. Sutterlin, et al., "A Biomechanical Evaluation of Cervical Spin Stabilization Methods in a Bovine Model: Static and Cyclical Loading," Spine, vol. 13, No. 7, pp. 795-802 (1988).
M. Grubb, et al., "Biomechanical Evaluation of Anterior Cervical Spine Stabilization," Spine, vol. 23, No. 8, pp. 886-892 (1998).

(Continued)

*Primary Examiner* — Pedro Philogene
*Assistant Examiner* — David Comstock
(74) *Attorney, Agent, or Firm* — Beem Patent Law Firm

(57) ABSTRACT

A device and method for anterior atlantoaxial stabilization may include one or more plates having a plurality of openings for receiving screws configured to screw into one or more C1 articular pillars, one or more C2 articular pillars, and the C2 body. A third cross-linking member may couple to first and second plates to provide additional rigidity and/or resistance to rotational forces. The cross-link member may be separate from one or both of the other plates. Alternatively, the cross-link member may be coupled, releasably or otherwise, to one or more of the other plates. Still further, one or more plates may be joined, e.g., via a single screw passing through openings in both plates or by making the device a unitary structure with a single, shared hole for the plates. One or more plates also may deviate from a substantially planar structure to better operatively engage the spinal features.

8 Claims, 4 Drawing Sheets

(56) References Cited

OTHER PUBLICATIONS

E. Morscher, et al., "Die vordere Verplattung der Halswirbelsaule mit dem Hohlschrauben-Plattensystem aus Titanium," Der Chirurg, vol. 57, No. 11, pp. 702-707 (1986).

A. Fayyazi, et al., "Chapter 8: Anterior/Posterior Cervical Instrumentation," in Complications of Spine Surgery: Treatment and Prevention (H. An & L. Jenis, editors), pp. 55-75 (2005).

R. Moftakhar, et al., "Anterior cervical plates: a historical perspective," Neurosurg Focus, vol. 16, No. 1, Article 8, pp. 1-5 (2004).

J. Gassman, et al., "The Anterior Cervical Plate," Spine, Medical Department, vol. 8, No. 7, pp. 700-707 (1983).

W. Caspar, et al., "Anterior Stabilization with the Trapezial Osteosynthetic Plate Technique in Cervical Spine Injuries," in Cervical Spine I (P. Kehr & A. Weidner, eds.), pp. 198-204 (1987).

Y. Koh, et al., "A Biomedical Comparison of Modern Anterior and Posterior Plate Fixation of the Cervical Spine," Spine, vol. 26, No. 1, pp. 15-21 (2001).

J. Vender, et al., "Fusion and instrumentation at C1-3 via the higher anterior cervical approach," J Neurosurg (Spine 1), vol. 92, pp. 24-29 (2000).

A. Vaccaro, et al., "Anterior C1-C2 Screw Fixation and Bony Fusion Through an Anterior Retropharyngeal Approach,"Orthopedics, vol. 22, No. 12, pp. 1165-1170 (1999).

C. Ulrich, et al., "Comparative Study of the Stability of Anterior and Posterior Cervical Spine Fixation Procedures," Archives of Orthopaedic and Traumatic Surgery, vol. 106, pp. 226-231 (1987).

J. Brown, et al., "Cervical Stabilization by Plate and Bone Fusion," Spine, vol. 13, No. 3, pp. 236-240 (1988).

J. Spivak, et al., "The Effect of Locking Fixation Screws on the stability of Anterior Cervical Plating," Spine, vol. 24, No. 4, pp. 334-338 (1999).

R. Louis, "Chirurgia anteriore del rachide cervicale superiore Anterior surgery of the upper cervical spine," La Chirurgia Degli Organi Di Movimento, vol. 77, No. 1, pp. 75-80 (1992).

R.Tippets, et al, "Anterior Cervical Fusion with the Caspar Instrumentation System," Neurosurgery, vol. 22, No. 6, Part 1, pp. 1008-1013 (1988).

R. Robinson, et al., "The Results of Anterior Interbody Fusion of the Cervical Spine," The Journal of Bone & Joint Surgery, vol. 44-A, No. 8, pp. 1569-1587 (1962).

R. W. Bailey, et al., "Stabilization of the Cervical Spine by Anterior Fusion," The Journal of Bone & Joint Surgery, col. 42-A, No. 4, pp. 565-594, 624, 1108 (1960).

J. Lu, et al., "Anatomic Considerations of Anterior Transarticular Screw Fixation for Atlantoaxial Instability," Spine, vol. 23, No. 11, pp. 1229-1236 (1998).

M. Cabanela, et al., "Anterior Plate Stabilization for Bursting Teardrop Fractures of the Cervical Spine," Spine, vol. 13, No. 8, pp. 888-891 (1988).

M. Aebi, et al., "Treatment of Cervical Spine Injuries with Anterior Plating: Indications, Techniques and Results," Spine, Symposium of Internal Fixation, vol. 16, No. 3S, pp. S38-S45 (1991).

M. Aebi, et al., "Indication, Surgical Technique and Results of 100 Surgically-treated Freactures and Freacture-dislocations of the Cervical Spine," Clinical Orthopeadics and Related Research, No. 203, pp. 244-257 (1986).

A. Vaccaro, et al., "Salvage Anterior C1-C2 Screw Fixation and Arthrodesis Through the Lateral Approach in a Patient With a Symptomatic Pseudoarthrosis," American Journal of Orthopedics, col. XXVI, No. 5, pp. 349-353 (1997).

R. Reindl, et al., "Anterior Instrumentation for Traumatic C1-C2 Instability," Spine, vol. 28, No. 17, pp. E329-E333 (2003).

R. Mobbs, et al., "Anterior Cervical Decompression and Fusion: Does the Addition of a Plate Reduce Axial Nexk Pain in the Short Term?" The Internet Journal of Spine Surgery, available at www.ispub.com/ostia/index.php?xmlFilePath=journals/ijss/vol2n2/fusion.xml, pp. 1-5, Feb. 19, 2008.

Spinal Technologies, Atlantis®, avilable at www.sofamordanek.com/patient-spinal-atlantis.html, pp. 1-2, Feb. 19, 2008.

Spinal Technologies, Atlantis Vision®, avilable at www.sofamordanek.com/atlantis-vision.html, pp. 1-2, Feb. 19, 2008.

Anterior Cervical Disectomy with Fusion, available at www.necksurgery.com/treatment-surgical-fusion.html, pp. 1-2, Feb. 19, 2008.

Anterior Cervical Plating Systems, available at www.medcompare.com/matrix/1477/Anteror-Cervical-Plating-Systems,html, pp. 1-3, Feb. 19, 2008.

T. Schnuerer, Cervical (Neck) Implants used in Spine Surgery, available at www.spineuniverse.com/displayarticle.php/article3576.html, p. 1, Feb. 19, 2008.

Trinica® and Trinica® Select Anterior Cervical Plate Systems, A New Twist to Anterior Cervical Plates, Zimmer Spine, Inc. Jun. 2005.

International Search Report and Written Opinion dated Jun. 26, 2009, issued in International Application No. PCT/US2009/043768 (13 pages).

\* cited by examiner

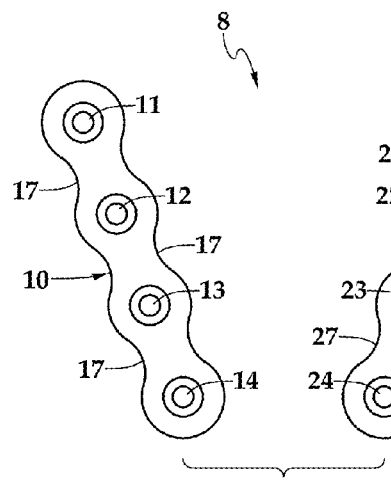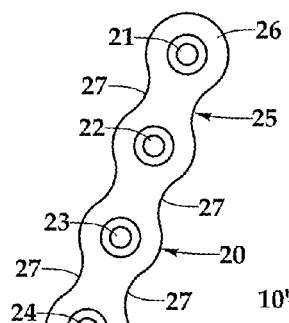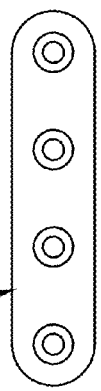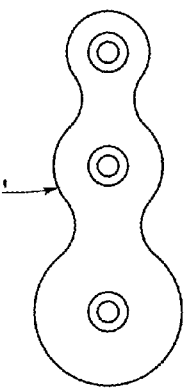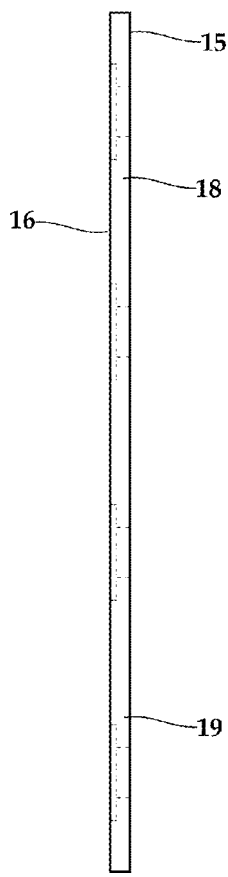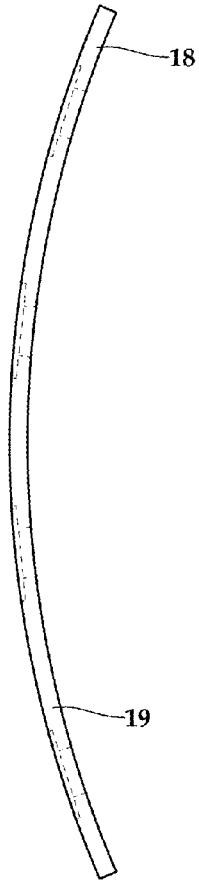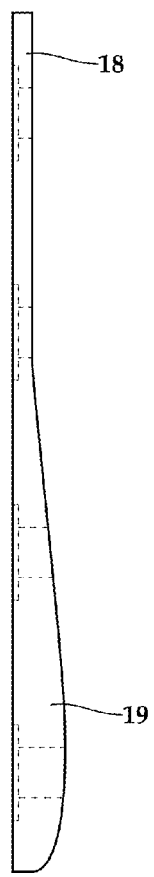
*Fig.1*  *Fig.3A*  *Fig.3B*
*Fig.2A*  *Fig.2B*  *Fig.2C*

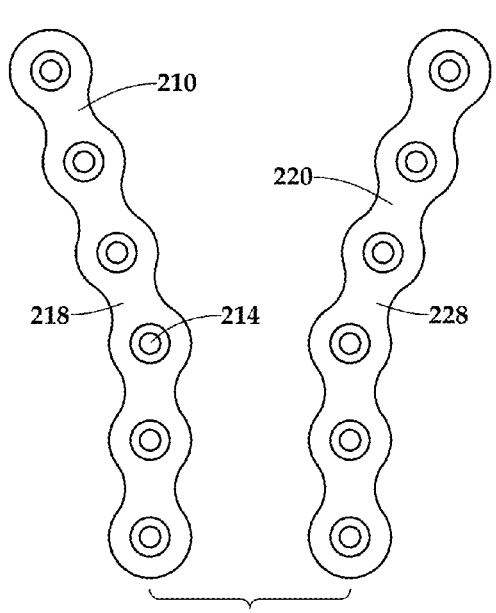
*Fig.10*
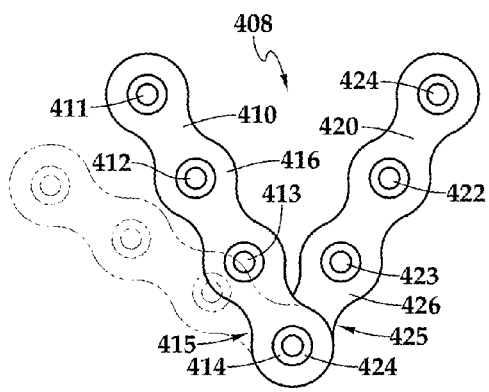
*Fig.14A*
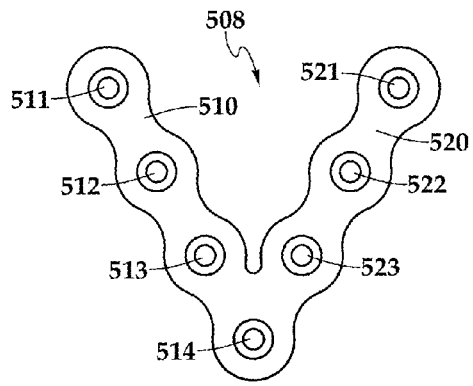
*Fig.14B*
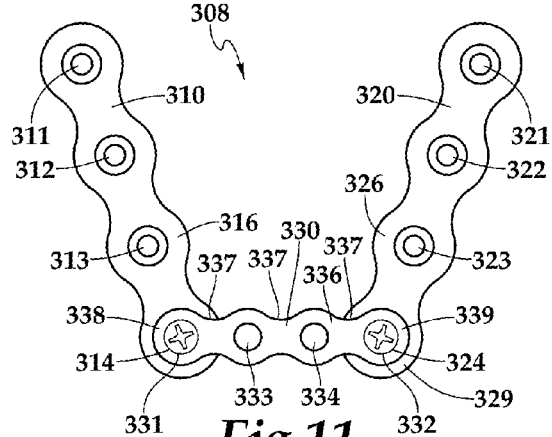
*Fig.11*
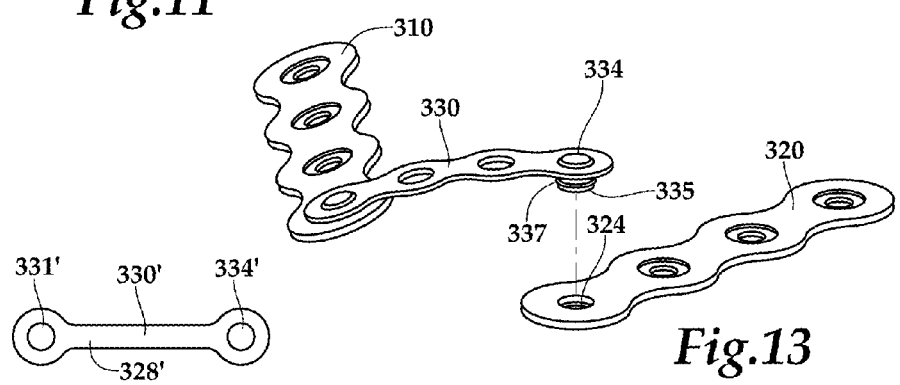
*Fig.12*
*Fig.13*

ANTERIOR ATLANTOAXIAL STABILIZATION BY LATERAL MASS SCREW FIXATION

This application claims the benefit of priority from U.S. Provisional Application 61/628,173, filed Oct. 26, 2011.

BACKGROUND OF THE INVENTION

1. Field of the Invention

The present invention pertains to a medical device and a medical procedure that will improve the safety, post-operative recovery, and ease of surgery to repair upper cervical spine (vertebral column, bones) damage.

2. Description of the Related Art

Traditionally, atlantoaxial region fixation has been performed from a posterior approach. Heretofore, anterior access has been available using transoral or transpalatal routes, which pose a high risk of infection. Furthermore, the instrumentation required for such anterior approaches is complex and not always available.

Anterior or high cervical approaches make it possible to expose the C1-C2 region, and such approaches have been used to perform excision of the odontoid process or tumors of the C2 or odontoid region. Nevertheless, stabilization of this region using previously available anterior methods requires a second stage operation, or a second operation, since there are no effective methods currently available for anterior fixation.

R. Reindl, et al., "Anterior Instrumentation for Traumatic C1-C2 Instability," *Spine*, vol. 28, pp. E329-33 discloses the use of an odontoid screw and anterior transarticular C1-C2 screws to instrument instability at this region. This approach requires the use of two high quality fluoroscopes, a radiolucent OSU fracture table, and a SynFrame retraction system. This approach is not a preferred surgical procedure and is seldom used today.

What is needed is a method and apparatus for atlantoaxial region fixation that overcomes the drawbacks described above.

BRIEF SUMMARY OF THE INVENTION

In one embodiment, a cervical spine fixation system may include: a first plate having a plurality of openings, including an opening configured to receive a screw for affixing the first plate to a first C1 articular pillar and at least one opening configured to receive a screw for affixing the plate to at least one of a first C2 articular pillar or the C2 anterior body; and a second plate having a plurality of openings, including an opening configured to receive a screw for affixing the second plate to a second C1 articular pillar and at least one of a second C2 articular pillar or the C2 anterior body. The first plate may include openings configured to receive screws for affixing the first plate to both the C2 first articular pillar and the C2 anterior body, and the second plate may include openings configured to receive screws for affixing the second plate to both the second C2 articular pillar and the C2 anterior body. In one embodiment, the plates also may include one or more openings configured to receive screws for affixing the plates to the C3 anterior body.

An upper portion of the first and second plates may include a twist about one or more axes, including a longitudinal axis. The twist about the longitudinal axis may be between about 10 degrees and about 40 degrees.

Holes on the plates may be substantially collinear, although one or more holes may deviate from collinearity if those holes are configured to receive screws to affix the plates to the C3 or lower vertebrae. The distance between the centers of adjacent holes may be between about 10 mm and about 15 mm, and in one embodiment, about 12 mm.

The fixation system also may include a third plate having a plurality of openings, including an opening configured to receive a screw for affixing the third plate to the first plate and to one of the C1 and C2 vertebrae and a second opening configured to receive a screw for affixing the third plate to the second plate and to one of the C1 and C2 vertebrae.

In another embodiment, a method of anterior fixation of a first cervical vertebra to a second cervical vertebra may include the steps of: (a) screwing a screw through a first opening in a first plate and into a first C1 articular pillar; (b) screwing a screw through a first opening in a second plate and into a second C1 articular pillar; (c) screwing a screw through a second opening in the first plate and into one of a first C2 articular pillar and the C2 anterior body; and (d) screwing a screw through a second opening in the second plate and into one of a second C2 articular pillar and the C2 anterior body. The method also may include the steps of screwing a screw through a third opening in the first plate and into the other of the first C2 articular pillar and the C2 anterior body; and screwing a screw through a third opening in the second plate and into the other of the second C2 articular pillar and the C2 anterior.

At least one of the first and second plates may be angled between 25° and 35° medially from a spinal midline, preferably about 30°. In addition, at least one of the openings for securing the first and second plates to their respective C1 articular pillars is placed between 1.5 cm and 2.0 cm from a spinal midline, preferably about 1.8 cm from a spinal midline.

The steps of screwing a screw through third openings in the first and second plates may comprise screwing a single screw through both third openings. Alternatively, the method may require, prior to steps (c) and (d), placing a third plate on top of the first and second plates, the third plate having a first opening configured to be disposed in line with the second opening on the first plate and a second opening configured to be disposed in line with the second opening on the second plate.

These and other features and advantages are evident from the following description of the present invention, with reference to the accompanying drawings.

BRIEF DESCRIPTION OF THE SEVERAL VIEWS OF THE DRAWINGS

FIG. 1 is a front view of one embodiment of a novel plate system having a plurality of plates each with a plurality of openings for contacting at least two vertebrae of the upper cervical spine.

FIG. 2A is a side view of one embodiment of one of the plates of FIG. 1.

FIG. 2B is a side view of a second embodiment of one of the plates of FIG. 1.

FIG. 2C is a side view of a third embodiment of one of the plates of FIG. 1.

FIG. 3A is a front view of a second embodiment of a plate for contacting at least two vertebrae of the upper cervical spine.

FIG. 3B is a front view of a third embodiment of a plate for contacting at least two vertebrae of the upper cervical spine.

FIG. 10 is a front view of another embodiment of a novel plate system having a plurality of plates each with a plurality of openings for contacting multiple vertebrae, including those of the upper cervical spine.

FIG. 11 is a front view of still another embodiment of a novel plate system having a plurality of plates each with a plurality of openings, including a cross-link member, for contacting multiple vertebrae, including those of the upper cervical spine.

FIG. 12 is a front view of another embodiment of a cross-link member.

FIG. 13 is an exploded, perspective view of one variation of the cross-link embodiment of FIG. 11, illustrating one type of connector between two plates.

FIG. 14A is a front view of yet another embodiment of a novel plate system having a plurality of plates each with a plurality of openings, for contacting multiple vertebrae, including those of the upper cervical spine.

FIG. 14B is a front view of a further embodiment of a novel plate system having a plurality of openings for contacting multiple vertebrae of the upper cervical spine.

DETAILED DESCRIPTION OF THE INVENTION

Figure 4:
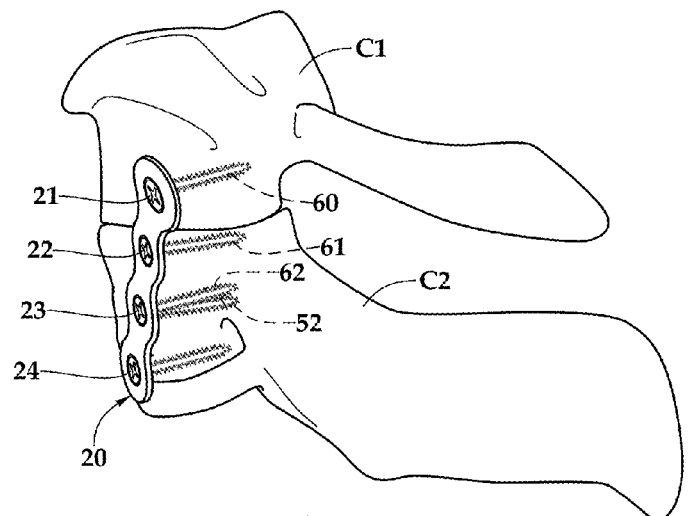
FIG. 4 is a perspective view of the plate system of FIG. 1, illustrated as installed on the C1 and C2 vertebrae.

A superior procedure for fixation of the atlantoaxial region, which reduces the complexity of this operation, while reducing the risk of infection, risk from repeated surgeries and anesthesia, and possible injury to arteries and nerve roots. This procedure utilizes an anterior approach and is superior to other procedures.

The new method utilizes a single surgical procedure, during which a novel medical device 8 comprising at least two small plates 10, 20 is attached by a plurality of screws, e.g., three screws per each atlantoaxial joint, as shown in one embodiment in FIG. 1. The screws attaching the metal plates are passed into the articular pillars of C1 and C2 on either side, and an additional screw may be placed into the vertebral body of axis (C2) as can be seen in FIGS. 2-3.

The embodiment of FIG. 1 includes a device 8 comprising a first plate 10 and a second plate 20. First and second plates 10, 20 may be substantially similarly shaped, e.g., first plate 10 may include a plurality of openings such as first opening 11, second opening 12, third opening 13, and fourth opening 14. Openings may extend through plate 10, from inward facing side 15 to outward facing side 16.

Similarly, second plate may include a plurality of openings such as first opening 21, second opening 22, third opening 23, and fourth opening 24, and these openings also may extend through plate 20, from inward facing side 25 to outward facing side 26. Although FIG. 1 shows an embodiment in which first and second plates each have four openings, either or both of plates 10, 20 may include a greater or lesser number of openings.

In one embodiment, both first and second plates 10, 20 may be substantially symmetrical, e.g., sides 15, 16 and 25, 26, respectively, may be substantially planar, such that either side may be used as the inward facing side and the other side may be used as the outward facing side. In another embodiment, inward facing sides 15, 25 may be slightly concave, which may allow plates 10, 20 to contour to one or more external surfaces of the C1, C2, and possibly C3 vertebrae.

Plates also may have a generally uniform thickness of between about 1 mm and about 2 mm, and in one embodiment about 1.5 mm. In one embodiment, plates may be generally planar when viewed in profile, as seen in FIG. 2A. Alternatively, plates 10, 20 may be generally concave from top to bottom when looking at inward facing side 15, as seen in FIG. 2B. In this embodiment, plates still may have a generally uniform thickness and further may have a radius of curvature of about 5 cm and about 25 cm.

In yet another embodiment, as seen in FIG. 2C, upper portion 18 of plate proximate at least first opening 11 may have a first thickness, which may expand to a second thickness when moving to lower portion 19 of plate proximate at least third and/or fourth openings 13, 14. Upper portion may have a thickness of about between about 0.5 and about 1.0 mm, preferably about 0.75 mm, expanding to about 1.5 mm at lower portion 19.

Returning to FIG. 1, openings 11-14 may be generally equally spaced from one another, e.g., between about 10 mm and about 15 mm apart, preferably about 12 mm apart. Openings 21-24 may be similarly spaced. For each plate 10, 20, openings 11-14 and 21-24, respectively, also preferably are generally collinear. Openings 11-14 and 21-24 additionally may contain one or more countersinks 11a-14a, 21a-24a configured to receive at least a part, and preferably at least substantially all, of each fastener head. Alternatively, openings 11-14 and 21-24 may not include countersinks.

One or both of plates 10, 20 may include side notches 17, 27 between holes, which may be sized and otherwise configured to receive staples for further securing plates. In one embodiment, notches 17, 27 may extend inward about 1 mm on each side of plate, i.e., narrowing plate by about 2 mm.

Plates 10, 20 may have a length between about 2 cm and about 6 cm, preferably between about 3 cm and about 5 cm, and in one embodiment, about 4 cm. Longer or shorter plates also may be used, depending on the size and spacing of the patient's vertebrae. For example, a plate for use with a child may be between about 3 and 4 cm long, whereas a plate for use with an adult may be between about 4 and about 6 cm long.

Plates 10, 20 may have a width between about 0.5 cm and about 2.5 cm, preferably between about 0.8 cm and about 1.5 cm. In one embodiment, plates 10' may have a generally constant width along their length, as seen in FIG. 3A. In another embodiment, plates may have a generally constant width along their length, with inward deviations formed by notches 17, 27, as seen in FIG. 1. In still another embodiment, one or both of plates 10, 20 may expand in width when moving from openings 11, 21 towards openings 14, 24, as seen in plate 10" in FIG. 3B. In this embodiment, plate 10" may expand between about 20% and about 75%, preferably about 50%. Alternatively, plate 10" may expand between about 0.2 cm and about 0.75 cm, preferably about 0.5 cm. In each embodiment, openings preferably are disposed substantially along a centerline of each plate.

Figure 5:
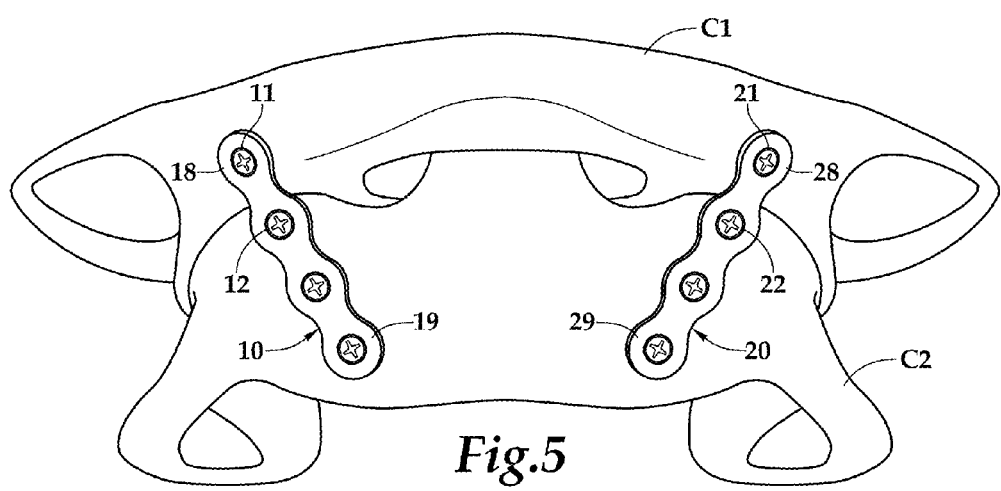
FIG. 5 is a front view of the installed embodiment of FIG. 1.

Turning to FIGS. 4-5, plates are placed in such a manner so that they converge medially on the C2 vertebral body to facilitate firm screw placement into the axis body, along with a screw placement into the articular facet of C2 superiorly. For each plate, a screw is placed into the C1 articular facet, another screw is placed into the C2 articular facet, and a third screw is driven into the body of the C2 vertebra. Preferably, screws are driven through uppermost openings, e.g., openings 11, 21 first, followed by driving screws through next openings 12, 22, etc., until screws are driven through bottom openings 14, 24. It will be appreciated that not all holes may receive screws but that, in any event, screws preferably are installed in a top-down fashion. Additionally, screws may be partially installed until all screws are partially installed or at least until all pilot holes are drilled, at which point screws may be fully tightened.

The plates lock the joint into place in such a manner that the plates diverge at C1 and converge at C2, giving an angled U- or V-shape to the construct. This design provides strength in reducing the most prominent motion component at the atlantoaxial joint, i.e., the rotation.

Figure 6A:
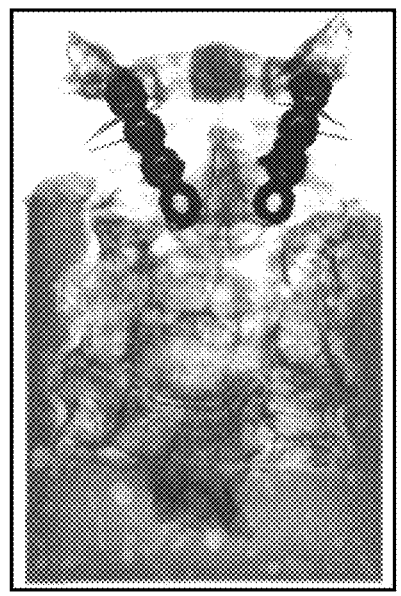
FIG. 6A is an x-ray top or anterior-posterior view illustrating the installation of the embodiment of FIG. 1.
Figure 6B:
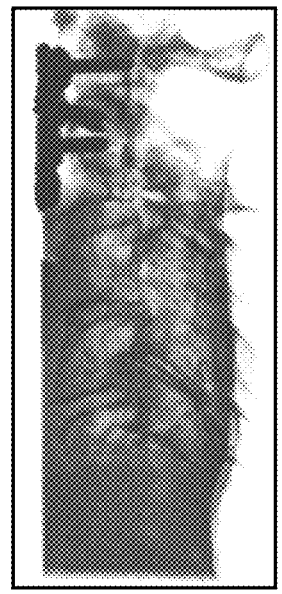
FIG. 6B is an x-ray side view or lateral projection illustrating the installation of the embodiment of FIG. 1.

This method is shown in FIG. 6, where x-rays of a specimen with the construct demonstrate the placement of the screws, the position of the plates, and the overall appearance at the end of the procedure. Note: FIG. 6A is the anterior-posterior view, and FIG. 6B is the lateral projection. As can be seen in FIGS. 4 and 6B, screws may be inserted generally perpendicular to each of plates 10, 20 or, alternatively, may be disposed at some other angle relative to inward facing and/or outward facing sides to a degree that provides for maximum engagement with portions of the intended vertebrae.

Screws 50-52, 60-62 may have heads sized slightly larger than their shanks, so as to allow heads to bear against plates 10, 20 when installed, but small enough so as to minimize material extending beyond plates 10, 20 or, preferably, to allow heads to seat flush against or recessed with respect to plates. For example, heads may be between about 1 mm and about 5 mm larger than shanks, preferably about 2 mm larger. Screws for engaging first vertebra may be sized differently than screws for engaging second or lower vertebrae. For example, screws 50, 60 may have heads having a diameter of about 1.5 mm and shanks having a diameter of about 1.3 mm. Screws 51, 52, 61, 62 may have heads having a diameter of about 2.2 mm and shanks having a diameter of about 2.0 mm. One or more of the screws also may taper from head to tip, either along its length generally or localized closer to the tip.

Openings for receiving fasteners to engage the first cervical vertebra, e.g., opening 11, may be between about 1 mm and about 2 mm in diameter, and in one embodiment, about 1.4 mm. Openings for receiving fasteners to engage the second or lower cervical vertebrae, e.g., openings 12, 13, 14 may be between about 1.5 mm and about 2.5 mm in diameter, and in one embodiment, about 2.1 mm. Alternatively, openings 11-14 may be sized slightly larger, e.g., between about 1 mm and about 3 mm larger, than major diameters of screws 50, 51, 52. Openings 11-14 also may be sized slightly smaller, e.g., between about 1 mm and about 3 mm smaller, than the heads of screws 50, 51, 52. Similar relationships may apply to openings and holes on other plates, e.g., second plate 20.

Figure 7:
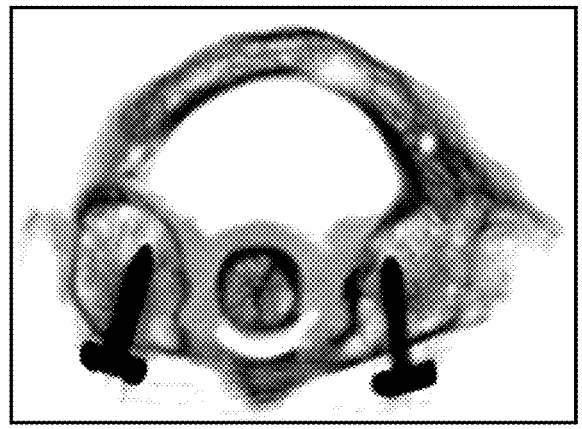
FIG. 7 is a CT scan top view illustrating the installation of the embodiment of FIG. 1 at the C1 facet.
Figure 8:
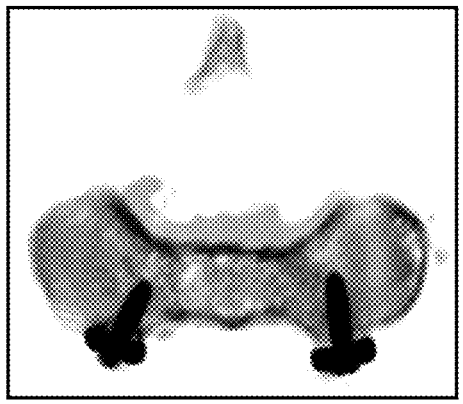
FIG. 8 is a CT scan top view illustrating the installation of the embodiment of FIG. 1 at the C2 facet.
Figure 9:
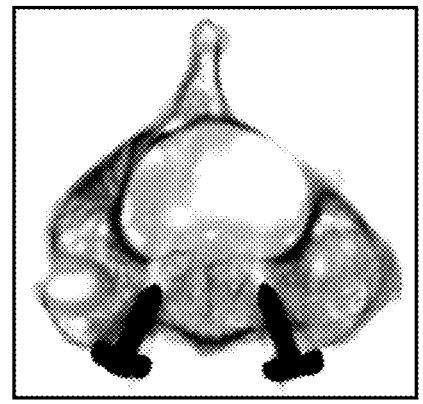
FIG. 9 is a CT scan top view illustrating the installation of the embodiment of FIG. 1 at the C3 facet.

FIGS. 7-9 are pictures of computerized tomographic scans taken at the C1 facet, the C2 facet, and the C2 vertebral body, respectively. These CT scan images show the location and placement of screws at each level of the spine.

The screws are inserted at a position that is between 1.5 cm and 2.0 cm from the midline with between 25° and 35° angulation medially. It was determined that the method described herein works best if the screws are placed in first openings 11, 21 at about 1.8 cm from the midline, with a 30° angulation medially.

The screws should be between about 5 mm and 20 mm in length, and different length screws may be used depending upon the vertebrae into which they are being screwed and/or the thickness of the material into which it is driven. In one embodiment, screws 50, 60 may be between about 8 mm and about 10 mm long, and screws 51, 52, 61, 62 may be between about 14 and about 18 mm long. In another embodiment, a different insertion location and/or angle allowed for a screw that was about 16 mm long being placed at the C1 articular facet, while a second screw that was about 14 mm long was placed at the C2 articular facet, and a third screw that was about 14 mm long fixated the plate to the body of the C2 vertebra. This design provides inherent strength in reducing rotation, the most prominent motion component at the atlantoaxial region.

In certain cases, it may not be possible or desirable to install one or more screws into the C2 facet, e.g., via screws 51, 61 in openings 12, 22. In these cases, anchoring device 8 still may provide sufficient anchoring via screws inserted into the C1 facet and the C2 body.

These procedures may be used following excision of an odontoid process, after the reduction of an atlantoaxial dislocation, and, in general, for the stabilization of C1 and C2. Most lesions at the craniovertebral junction (C1, C2) can be effectively treated by this method, even after excision of the anterior arch of the atlas. While prior reported methods for stabilizing C1 and C2 require a second operation or a second phase of the operation, this method does not require either a second operation or second stage procedure.

Another concern when stabilizing C1 and C2 is that there is a risk of injury to the vertebral artery and to the nerve roots. Injury to the vertebral artery and trauma to nerve roots are not uncommon when using existing methods of fixation using posterior transarticular screws. Because of the superior anatomical access using this anterior approach these two risks are minimized.

In addition, one of the post-operative adverse effects of posterior methods is that often there is severe restriction of neck movement due to the operative exposure and the stiffness of the construct used. Due to the biomechanics involved in the construct used herein, neck pain, stiffness, and restricted neck movement will be less severe.

The novel approach taught herein overcomes many of the difficulties encountered with other C1-C2 fixation methods. For example, the anterior approach is more anatomically beneficial because it is performed while the patient is in a supine position, i.e., the normal anatomical position of the human body. The existing posterior approaches are performed while the patient is in a prone position, which may cause neurological damage while positioning the patient.

Further, since this technique combines both decompression and stabilization in a single operation, it eliminates a second stage or a second operation of posterior fixation. This second phase must be accomplished by decompression of the spinal canal or reduction of atlantoaxial instability, and then later by fixing the joints that are visualized.

Because of its superior anatomical approach (in the supine position) with direct visualization of the bony mass utilized for placement of the implant, the risk of injuries to the vertebral artery and venous structures are significantly reduced. Also, for the same reasons, there is very little risk of injury to neural structures like nerve roots. Another improvement over existing methodology and implants is that the use of this new method will result in less stiffness and rigidity of the neck, particularly when compare with the most rigid fixation, such as posterior transarticular screws.

Other design shapes and sizes of the plate may be used, e.g., a single metallic V-shaped implant or a pair of implants. This approach also may be used for percutaneous or endoscopic placement of a construct. Further, odontoid fractures, congenital or primary reducible, and atlantoaxial dislocation may be successfully treated with this method.

Moreover, while the description above has referred primarily to fixation of the device to the C1 and C2 vertebrae, the device also may be affixed to other cervical vertebrae, primarily including C3 and potentially C4. For these extended embodiments, several variations are possible. For example, one embodiment of an extended plate may include additional openings generally collinear with openings 11-14.

In another embodiment, as seen in FIG. 10, plate 210 may include a bend 218 after opening 214 to follow the path of the spine, so as to allow for screws to screw into the body of one or more additional vertebrae. Plate 220 may include a bend 228 with a similar, albeit mirror-imaged, angle. The angle between portions of plate 210 and/or 220 may be between 25° and 35°, preferably about 30°.

Turning to FIG. 11, another embodiment of device 308 is shown. Like numerals as compared to the first embodiment described herein, but with a 300s prefix, refer to similar elements in this embodiment. In this embodiment, device 308 may include a first plate 310, a second plate 320, and at least a third plate 330. First plate 310 may include openings 311-314 configured to receive screws to affix plate 310 to a C1 articular facet, a C2 articular facet, and the body of the C2 vertebra. Similarly, second plate 320 may include openings 321-324 configured to receive screws to affix plate 320 to the other C1 articular facet, the other C2 articular facet, and the body of the C2 vertebra.

Third plate 330 may include a plurality of openings, including at least openings 331, 332. Openings 331, 332 may be spaced such that, in use, they overlay a complementary pair of openings on plates 310 and 320, e.g., openings 313 and 323. Additionally or alternatively, third plate may include additional openings such as openings 333, 334, which may be configured to overlay, e.g., openings 314, 324 on plates 310, 320. Openings 331, 332 also may be configured to overlay openings 314, 324, depending on spacing between plates 310, 320. In this manner, a surgeon may be able to position third plate 330 at a desired location to achieve the desired degree of fixation.

Plate 330 may be considered a cross-linking member that supplements fixation provided by plates 310, 320. As such, plate 330 may be generally as thick as or, preferably, thinner than plates 310, 320. For example, plate 330 may have a thickness between 1.0 mm and 1.5 mm, preferably about 1.2 mm.

In one embodiment, plates 310, 320 may have substantially planar outward facing sides 316, 326, and plate 330 may rest on top of, and extend away from plates 310, 320. In another embodiment, a portion of plates 310, 320 may be recessed relative to other portions of outward facing sides 316, 326, such as within lower portion 329 of plate 320. The degree of recess may be less than or generally equal to a thickness of plate 330 such that outward facing side 336 of plate 330 may be generally level to outward facing sides 316, 326 of plates 310, 320 or at least partially recessed.

In this embodiment, device 308 may include one or more cross-linking members, such as third plate 330. For example, as described above, device 308 may include one cross-linking member configured to receive fasteners that also pass through openings 313, 323 or 314, 324. In another example, device 308 may include a first cross-linking member, e.g., overlaying openings 313, 323 and a second cross-linking member, e.g., overlaying openings 314, 324. The cross-linking members may include a plurality of openings configured to permit those members to be joined to plates 310, 320 at multiple sets of openings.

Alternatively, one or more cross-linking members may be configured to join to a wider-spaced set of openings on plates 310, 320 but not to a more narrowly-spaced set of openings. For example, device 308 may include a cross-linking member having openings configured to overlay openings 313, 323 but not have openings configured to overlay more closely-spaced openings 314, 324. This may prevent the ends 338, 339 of the cross-linking member from extending a significant distance outward beyond the first and second plates 310, 320 proximate the region of connection with the cross-linking member.

Like plates 310, 320, plate 330 may include one or more sets of notches 337 spaced between one or more sets of openings. As seen in FIG. 11, plate 330 may include a notch 337 between each set of adjacent openings. In both plate 330 and the other plates of the various embodiments described herein, notches may be formed by intersecting one or more circles that are substantially co-centric with the openings.

Turning to FIG. 12, a second embodiment of plate 330' is shown. Plate 330' may include openings 331' and 334' but not additional openings. Instead, plate 330' may include a cross-bar member 328' between openings 331' and 334'. Member 328' may have a generally constant width along its length. That width preferably is less than a width of the rest of plate 330' and may be between the plate width and the diameter of openings 331', 334'. Like plate 330, plate 330' may be between about 3 cm and about 4 cm long.

In one embodiment, plate 330 may be a separate, distinct member from one or both of plates 310, 320. In another embodiment, plate 330 may be joined to one or both of plates 310, 320 prior to insertion of any fasteners. For example, FIG. 13 shows an embodiment in which plate 330 includes a tab or other protrusion 335 extending downward around a perimeter of opening 324. Protrusion 335 may be configured to fit within opening 324 to prevent relative translation of plates 320, 330 when a screw is not inserted into openings 324, 334. Plate 330 also may include a coupler 337 to make separation of plates 320, 330 more difficult. In FIG. 13, coupler 337 may comprise a bead or enlarged diameter portion on protrusion 335, which may engage an underside of plate 320 or a bead within opening 324. Other types of couplers are possible to provide fixed or releasable attachment between plates 320, 330.

In the embodiment of FIG. 13, plate 330 may include a similar coupler in order to couple to plate 310. When coupled, plates may allow for pivoting or relative rotational movement to achieve a desired positioning during use. Alternatively, plate 330 may not include a similar coupler to couple to plate 310 but instead may rest on top of plate and may be able to translate relative to plate 310 prior to insertion of a screw into opening 331 and one of the openings on plate 310. It will be appreciated that, similarly, plates 310, 330 may be couplable while plate 320 may be free to translate.

Turning now to FIG. 14A, another embodiment of fixation device 408 is shown. In this embodiment, device 408 again may include a first plate 410 with openings 411-414 and a second plate 420 with openings 421-424. However, instead of a gap at a lower pair of openings 414, 424, e.g., overlaying the C2 body, openings 414, 424 may substantially overlap, such that a single fastener may be driven through openings 414, 424 to affix plates 410, 420 to cervical vertebra.

Plates 410, 420 may be separate elements, joined but separable, or joined but inseparable elements. In each case, plates 410, 420 may be pivotable or otherwise adjustable relative to one another to allow the surgeon to select the desired angle of installation.

In order to accomplish this overlay of plates 410, 420, one of the plates may rest on top of the other, proximate openings 414, 424 (or whatever openings employ a common screw). If, as described above with respect to another embodiment, plates are generally linear or inward and outward facing sides are generally planar or have substantially uniform surfaces, the plate on top here may not rest on cervical vertebrae along its length or at points underneath one or more openings. This spacing may require the use of longer screws and/or shims for affixing that plate at these cervical portions.

Preferably, however, one of plates may be considered a "bottom" plate, e.g., plate 420, while the other plate 410 may be designated a "top" plate. The top plate may include a recessed portion along its inward facing side 415. Recessed portion may surround at least opening 414, thereby allowing inward facing side 415 to be disposed closer to vertebral surfaces. Additionally or alternatively, bottom plate 420 may include a similarly-sized recessed portion along its outward facing side 426 surrounding at least opening 424. As such, when top plate 410 is place on top of bottom plate 420, the inward facing surfaces 415, 425 of both plates (with the exception of the surface of the top plate in the area that is resting on the bottom plate) may substantially abut vertebral surfaces. Similarly, the outward facing surfaces 416, 426 of both plates (with the exception of the surface of the bottom plate in the area that is underneath the top plate) may be substantially aligned.

Turning to FIG. 14B, another embodiment of a device 508 is shown. This embodiment shows a single, unitary design having plates 510, 520 that are joined in a V-shaped configuration at the base. In this embodiment, plate 510 may include openings 511, 512, 513 and plate 520 may include openings 521, 522, 523. Instead of a plurality of fourth openings, however, device 508 may include a single opening 514 at the junction of plates 510, 520. Arms 510, 520 may be angled between about 15 degrees and about 45 degrees with respect to the centerline, preferably between about 20 degrees and about 30 degrees, and in one embodiment, about 30 degrees.

Each of the plates described above may be configured to rest generally flush against the vertebral surfaces when installed. As seen in FIG. 13, cross-link plate 330 may include a radius of curvature along its length. Radius may be selected, e.g., to permit plate 330 to rest generally on the C2 anterior body. In one embodiment, plate 330 is pre-formed with the appropriate radius of curvature. In another embodiment, plate 330 may be substantially rigid but may be deformable either manually or with tools to form plate 330 into a desired configuration to customize it for each patient.

Similarly one or both of the other plates may include one or more twists to allow those plates to rest on surfaces of multiple vertebrae. For example, as seen in FIGS. 4 and 5, plates 10, 20 may contact portions of the C1 articular facet and C2 body that lie in different planes. Plates 10, 20 may include a twist, e.g., between openings 11, 12 and 21, 22, respectively. Twist may cause upper portions 18, 28 of plates to lie in offset planes from lower portions 19, 29 of plates. Upper portions of plates may be rotated about one or more axes of rotation, preferably including the longitudinal axis of each respective plate. A degree of rotation in the twist may be between about 10 degrees and about 40 degrees, and in one embodiment, about 20 degrees. Twist may allow for the upper portions 18, 28 to be more medially facing, while plates 10, 20 may curve gently to become straight on the anterior surfaces of the C2 and, potentially, lower vertebrae. In addition to allowing plates 10, 20 to rest more flush against vertebral surfaces, twists also may orient openings to allow screws to be driven into thicker portions of articular facets or vertebral bodies, which may allow for more secure engagement and increased stabilization. As with the curvature in plate 330, plates 10, 20 may be pre-formed with twists or, alternatively, may be provided to the surgeon in a substantially planar configuration, allowing for the surgeon to customizably deform each plate for the patient.

The curvatures or deformations described above with respect to the embodiments of FIGS. 13 and 4-5 also may apply similarly to each of the other embodiments described herein.

The plates can be made of any bio-compatible material, but the preferred material is titanium. The approach taught here is not limited to the use of titanium or other bio-compatible metals. It is expected that the application of biodegradable constructs or implants, or the application of constructs or implants that comprise other biocompatible, non-metallic materials, other than or in addition to titanium, would further improve the versatility of this method of fixation, since rigidity and stiffness of the neck from the construct would be completely eliminated.

In order to test this novel method of fixation using the novel device, a number of experiments were conducted on cadaver cervical spines. For these experiments, the tests were done under controlled experiment conditions. Cervical spines of eight individual cadavers with an average age of 79 years were tested. The actual age of these persons ranged between 61 and 91 years (median of 84, with a standard deviation of 11 years). Of those tested, 6 were male and 2 were female, and all were Caucasian.

All spines tested were harvested from unembalmed cadavers. After these cervical spines were harvested, most of the soft tissue was removed from C1, C2, and C3 levels, leaving ligaments and joint capsules in place. During this process, care was taken to avoid destabilizing the facets joining C1 and C2. Transarticular screws facilitated the fusion of C1 to C2. The C3 level was encased in automobile body filler (BONDO) using a polyethylene mold. After encasement, the polymer was allowed to cure overnight before testing. Some of these encased spines were frozen and kept in that state until the day prior to testing. On the day of testing each specimen was allowed to assume room temperature.

In order to induce instability of C1-C2 articulation, cuts were made to the joints bilaterally. This thickness of the articular mass of C1 was measured on the axial CT scan slices to be 1.8" anterior posterior and 1.3" transverse dimensions. The facet surface available for screw entry was identified to be 1.8 cm from the midline of the spine, with a 30 degree angulation medially. The stabilizing plates were located such that they converged medially on the C2 vertebral body, which facilitated insertion of a screw into the axis body, and a second screw into the articular facet of the C2 superior to this screw. A 16 mm long screw was placed into the C1 articular facet. A second screw, 14 mm long, was inserted into the C2 articular facet, and a third screw, 14 mm long, was driven into the C2 vertebral body. Locking plates were used diverging at the C1 and converging at C2, giving a V-shape to the construct, stabilizing the joint bilaterally (see FIG. 1). This design provided inherent strength to the repaired joint by reducing the most prominent motion at the atlanto-axial joint, i.e., the rotation.

Five modes of testing were conducted to simulate the normal range of cervical spine motion at C1 and C2, both before and after application of the construct. The modes included rotation, flexion, extension, lateral bending to the right side, and lateral bending to the left side. Rotational mechanical testing was conducted on an Instron 8874 (Instron Corp., Canton, Mass.) bi-axial testing frame, and the data were acquired through a custom program in LabView (National Instruments, Austin, Tex.). The data were controlled and acquired on a computer, and the results were plotted using Microsoft Excel. Statistical analysis was done using the Student t-test (Sigmastat, v. 3.2).

Results of these tests are given below in Table 1 (p-value is assumed to be significant at a value <0.05).

| Movement Tested | Intact | Plated | Normalized | P-value |
|---|---|---|---|---|
| Rotation, N-m/deg | 0.36 | 1.07 | 3.38 | 0.004 |
| Bending left to right, N/mm | 38.41 | 55.91 | 1.68 | 0.05 |
| Bending right to left, N/mm | 48.37 | 61.25 | 1.53 | 0.3 |
| Flexion, N/mm | 44.02 | 60.56 | 1.44 | 0.1 |
| Extension, N/mm | 46.10 | 51.82 | | 0.7 |

These results show that there was significant reduction in rotation at C1 and C2 after the screw plate fixation. Though bending showed some reduction, the construct did not cause a significant reduction of flexion and extension. These results mean that neck stiffness and rigidity would be far less after the procedure than they would be using any other existing approaches. This reduction in neck stiffness and the reduction of neck rigidity are significant advantages over prior techniques.

In order to apply this method to living persons, physicians will make a high cervical incision to reach the atlantoaxial region, in order to expose the joints on both sides, under general anesthesia. The patient would be positioned with a slight neck extension with head turned to one side. Two plates would be fixed as described above and then the incision would be closed in a routine fashion. Bone graft harvested from the patient or synthetic bone substitutes would be utilized around the joint and on either side of the plates to promote new bone growth (promoting natural fusion and bone growth).

The complete disclosures of all references cited in this Specification are hereby incorporated by reference. In the event of an otherwise irreconcilable conflict, however, the present specification shall control.

While the foregoing written description enables one of ordinary skill to make and use what is considered presently to be the best mode thereof, those of ordinary skill will understand and appreciate the existence of variations, combinations, and equivalents of the specific exemplary embodiments and methods herein. The invention should therefore not be limited by the above described embodiments and methods, but by all embodiments and methods within the scope and spirit of the invention as claimed.

What is claimed is:

1. A method of anterior fixation of a first cervical vertebra to a second cervical vertebra, comprising:
    (a) screwing a screw through a first opening in a first plate and into a first articular pillar of the first cervical vertebra;
    (b) screwing a screw through a first opening in a second plate and into a second articular pillar of the first cervical vertebra;
    (c) screwing a screw through a second opening in the first plate and into one of a first articular pillar and the anterior body of the second cervical vertebra; and
    (d) screwing a screw through a second opening in the second plate and into one of a second articular pillar and the anterior body of the second cervical vertebra.

2. The method of claim 1, further comprising:
    screwing a screw through a third opening in the first plate and into the other of the first articular pillar and the anterior body of the second cervical vertebra; and
    screwing a screw through a third opening in the second plate and into the other of the second articular pillar and the anterior body of the second cervical vertebra.

3. The method of claim 1 wherein at least one of the first plate and the second plate is angled between 25° and 35° medially from a spinal midline.

4. The method of claim 1 wherein at least one of the first plate and the second plate is angled 30° medially from a spinal midline.

5. The method of claim 1, wherein at least one of the opening for securing the first plate to the first articular pillar of the first cervical vertebra and the opening for securing the second plate to the second articular pillar of the first cervical vertebra is placed between 1.5 cm and 2.0 cm from a spinal midline.

6. The method of claim 1, wherein at least one of the opening for securing the first plate to the first articular pillar of the first cervical vertebra and the opening for securing the second plate to the second articular pillar of the first cervical vertebra is placed about 1.8 cm from a spinal midline.

7. The method of claim 1, wherein the step of screwing a screw through a third opening in the first plate and the step of screwing a screw through a third opening in the second plate comprise screwing a single screw through both third openings.

8. The method of claim 1, further comprising the steps of:
    prior to steps (c) and (d), placing a third plate on top of the first and second plates, the third plate having a first opening configured to be disposed in line with the second opening on the first plate and a second opening configured to be disposed in line with the second opening on the second plate.

* * * * *